(12) United States Patent  
Kafai El-Khorassani

(10) Patent No.: US 8,366,626 B2  
(45) Date of Patent: Feb. 5, 2013

(54) SIMPLIFIED FRONTO-SAGITTAL AND TWO-DIMENSIONAL ULTRASOUND APPARATUS EXCLUSIVELY INTENDED FOR TEMPORO-MANDIBULAR ARTICULATIONS (ATM)

(76) Inventor: Hossein Kafai El-Khorassani, Luxembourg (LU)

( * ) Notice: Subject to any disclaimer, the term of this patent is extended or adjusted under 35 U.S.C. 154(b) by 259 days.

(21) Appl. No.: 12/664,772

(22) PCT Filed: Aug. 27, 2007

(86) PCT No.: PCT/IB2007/002444  
§ 371 (c)(1),  
(2), (4) Date: Dec. 15, 2009

(87) PCT Pub. No.: WO2009/027754  
PCT Pub. Date: Mar. 5, 2009

(65) Prior Publication Data  
US 2010/0198069 A1    Aug. 5, 2010

(51) Int. Cl.  
*A61B 5/00* (2006.01)  
*A61B 8/00* (2006.01)  
*A61C 19/04* (2006.01)  
(52) U.S. Cl. ........... 600/459; 600/437; 600/443; 433/68  
(58) Field of Classification Search .................. 600/407, 600/437, 443, 459, 590; 433/25, 29, 68, 433/69  
See application file for complete search history.

(56) References Cited

U.S. PATENT DOCUMENTS

| | | | | |
|---|---|---|---|---|
| 5,781,273 | A * | 7/1998 | Boden ............................ | 351/156 |
| 7,285,093 | B2 * | 10/2007 | Anisimov et al. ............. | 600/443 |
| 2003/0204150 | A1 * | 10/2003 | Brunner ......................... | 600/590 |

* cited by examiner

OTHER PUBLICATIONS

English Translation of Hossein (FR 2806611, Sep. 25, 2001) provided by EPO.*

*Primary Examiner* — Long V. Le  
*Assistant Examiner* — Katherine Fernandez  
(74) *Attorney, Agent, or Firm* — James E. Walton; Richard G. Eldredge

(57) ABSTRACT

The invention relates to a simplified fronto-sagittal and two-dimensional ultrasound apparatus exclusively intended for the exploration of the two right and left temporo-mandibular articulations (ATM) at rest or during mandibular movement, in the case of stomatology and traumatology exams. The calculation and the adjustment of the parameters for obtaining a displayed image of the region of the temporo-mandibular articulations is already done during the design step. Accordingly, the invention provides an apparatus with small dimensions and a lower cost relative to traditional ultrasound apparatuses, which will promote its use in medical practices both from a logistic and financial point of view. This exploration method has a low cost, does not require any particular preparation or hospitalisation for the patient, does not include any risks due to X-rays, and has no known side effects. The apparatus includes a quadruple hinged ultrasound probe (right and left) (FIG. 3, n°1 et n°3), two of which are connected to a flexible and telescopic extra-oral and semi-circular bearing (FIG. 3, n°2) and are placed around the head of a patient, while two other ones are connected to a flexible and telescopic intra-oral and semi-circular bearing (FIG. 3, n°4) adapted to the upper jaw. The bearings are connected to a screen (FIG. 3, n°5) for simultaneously displaying the right and left ATM and for comparing them both in the sagittal and frontal planes. A printer (FIG. 3, n°6) can be used for reproducing the selected images on paper. The device of the invention is particularly intended for use in medical practices and in hospital stomatology and traumatology wards for instantaneously displaying the temporo-mandibular articulations.

12 Claims, 2 Drawing Sheets

SIMPLIFIED FRONTO-SAGITTAL AND TWO-DIMENSIONAL ULTRASOUND APPARATUS EXCLUSIVELY INTENDED FOR TEMPORO-MANDIBULAR ARTICULATIONS (ATM)

The present invention relates to a novel simplified apparatus for fronto-sagittal and two-dimensional echography. Indeed, it is pre-designed exclusively for exploring temporo-mandibular joints (TMJs) in the case of stomatological and traumatological examinations.

In order to achieve this, all the different parameters required for viewing the examined region have already been pre-established and adjusted during its industrial design, at the frontal plane and at the sagittal plane of temporo-mandibular joints.

Conventional echography apparatuses are actually very elaborated because of the possibility which is provided for adjusting the different viewing parameters depending on the anatomical region to be observed, which requires elaboration of an adjustment system, involving a considerable increase in the size and cost of the apparatus. This will not be the case of the apparatus proposed above, since it is exclusively intended for TMJ examination and therefore does not require any adjustment.

Thus, we shall have available a small size and less expensive apparatus which will allow generalization of its application in medical practices, notably financially. With the apparatus, it is possible to directly and instantaneously obtain images of the TMJ at rest, but especially during their movement.

TMJ examination by conventional medical imaging: for example panoramic radiography (orthopantomogram), does not allow viewing of this dual joint in motion. This is a handicap in examining articular pathology. Further, the cost of an autopantomogram apparatus is considerable and does not allow generalization of its use in medical practices.

"MRI cinema" (examination by Nuclear Magnetic Resonance) allows moving organs to be viewed as in echography. But because of its high cost, only certain specialized hospitals may exclusively be equipped with this apparatus.

With other medical imaging systems, it is not possible to examine moving TMJs. These are:
  tomographic radiography;
  arthrography;
  (standard and three-dimensional) tomodensitometry
  MRI;

Apart from MRI and "MRI cinema", the other imaging systems resort to X-rays (ionizing radiation) which is not the case of an examination by echography. This latter point is essential because it allows repetition of MTJ examinations in order to better study the topography of the region in the different mandibular movements (TMJ functional examination), without any inconvenience for the patient, notably for pregnant women who should not be exposed to X-rays.

DESCRIPTION OF THE APPARATUS

Figure 1:
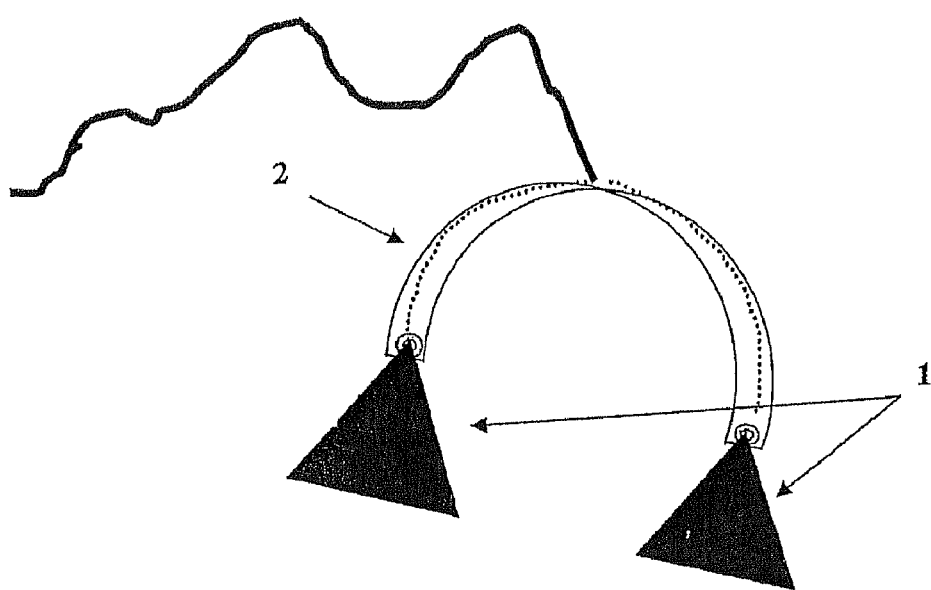
Figure 2:
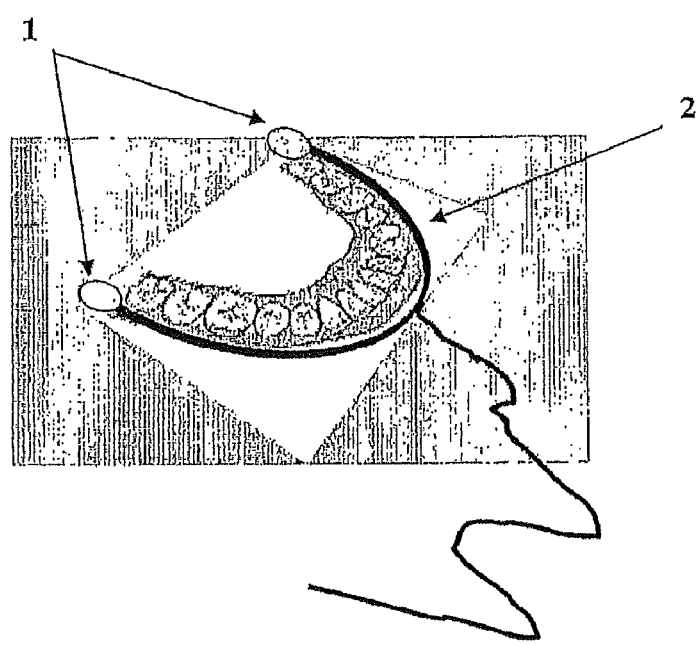
Figure 3:
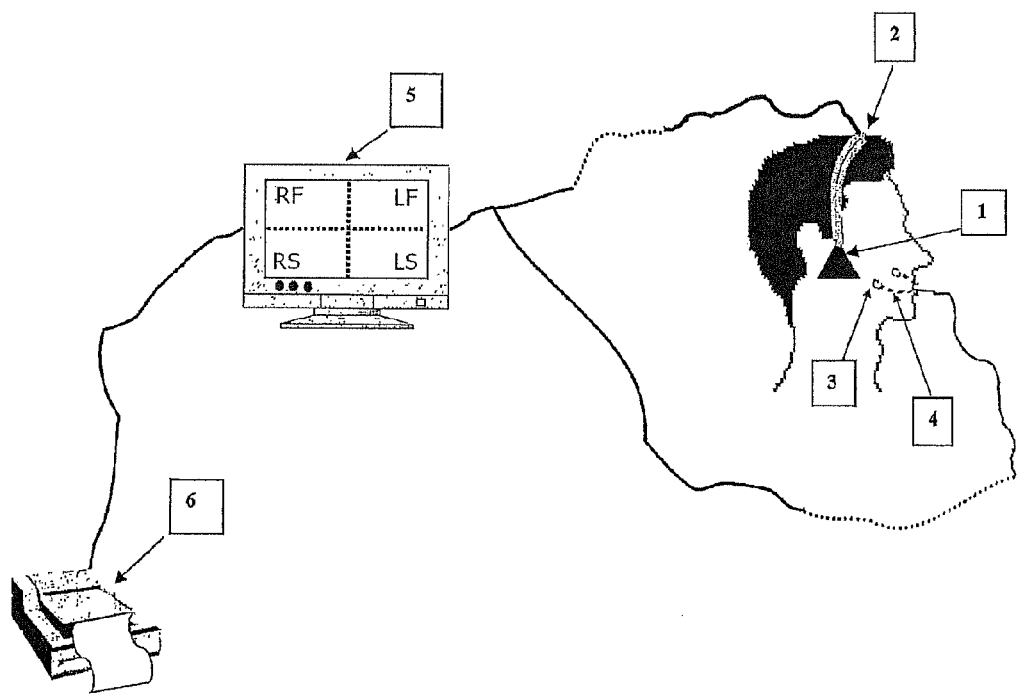

The apparatus consists of 5 components:
1. A dual extra-buccal (right and left) ultrasonic probe (FIG. 1, no.1) sending high frequency (small wavelength) molecular impact waves in the saqittal plane. These are acoustic waves which are not perceivable by the ear, just as conventional echography apparatuses but pre-adjusted exclusively for the temporo-mandibular joints (TMJs) in the sagittal plane; the dual probe is mandatory because the mandible has a dual joint (right TMJ and left TMJ);
2. A telescopic extra-buccal flexible semicircular support (FIG. 1, no.2) on which the two probes are attached. It is fitted around the head of the patient since it is flexible. The probes are jointed with this support at their junction. They are placed in front of the two external auditory ducts while keeping contact with the skin. The semicircular support is adjustable in height and should therefore be telescopic;
3. A dual intra-buccal (right and left) ultrasonic probe in contact with the mucosa of the retromolar region of the upper jaw (FIG. 2, no.1) bound by an intra-buccal flexible semicircular support which may be fitted to the upper jaw, sending high frequency (small wavelength) molecular impact waves in the frontal plane. These are acoustic waves which are perceivable by the ear, just as for conventional echography apparatuses, but exclusively pre-adjusted for the region of temporo-mandibular joints (TMJs) in the frontal plane. The dual probe is mandatory since the mandible has a dual joint (right TMJ and left TMJ);
4. A telescopic maxillary intra-buccal flexible semicircular support (FIG. 2, no.2) on which the two probes are attached. This flexible support is fitted around the upper jaw and is telescopic. Both intra-buccal probes are in contact on the mucosa of the retromolar region of the upper jaw. Both of these probes are attached at the end of this intra-buccal semicircular support;
5. A screen (FIG. 3, no.5) which allows simultaneous viewing of the right and left TMJs in the sagittal plane and in the frontal plane. This simultaneous viewing allows a comparison between the right TMJ and the left TMJ. This screen is connected to the two semicircular supports by two electric wires. The screen is laid on the work table and is provided with a volatile memory which allows selective recording of the images. The screen is connected to a printer (FIG. 3, no.6) which allows the recorded images to be reproduced on paper;

Principle of Exploitation of the Region to be Studied

This is a fronto-sagittal and two-dimensional echography apparatus as opposed to unidimensional echography (not very used because it only shows the structures encountered by the beam of use, along a straight line).

The four probes are provided with an ultrasonic transmitter (acoustic waves which are not perceived by the human ear). The reflected waves (radar principle) are then transformed into electronic signals in order to view the relevant region (principle of conventional two-dimensional echography apparatuses).

In order to promote transmission of the ultrasonic waves in the anatomical region to be studied, the surfaces will be coated with gel beforehand (principle of external echography).

The apparatus according to the invention is exclusively intended for exploring right and left temporo-mandibular joints simultaneously, and in the sagittal plane as well as in the frontal plane.

The invention claimed is:
1. A fronto-sagittal and two-dimensional echography apparatus, comprising:
  an extra-buccal skull support configured to fit partially around a head of a user;
  two extra-buccal ultrasonic probes attached to the skull support, the extra-buccal ultrasonic probes being con- figured to send and receive high-frequency molecular impact waves solely into the sagittal plane of a user's temporo-mandibular joints;

an adjustable intra-buccal maxillary support configured to adjustably fit within a mouth of the user; and two intra-buccal ultrasonic probes attached to the maxillary support, the intra-buccal ultrasonic probes being configured to send and receive high-frequency molecular impact waves solely into the frontal plane of the user's temporo-mandibular joints, the two intra-buccal ultrasonic probes being configured to come in contact with a mucosa region of a retromolar region of an upper jaw.

2. The echography apparatus according to claim 1, further comprising:

a display system for receiving, recording, and simultaneously displaying views of the user's left and right temporo-mandibular joints in both the frontal plane and the sagittal plane.

3. The echography apparatus according to claim 1, wherein the ultrasonic probes are pre-adjusted to analyze only a region of the user's left and right temporo-mandibular joints.

4. The echography apparatus according to claim 1, wherein the extra-buccal probes are joined to the skull support so as to be disposed in front of both of a user's external auditory ducts by about 2 cm, and to maintain contact with the user's skin.

5. The echography apparatus according to claim 1, wherein the intra-buccal probes are joined to the maxillary support so as to be in contact with the mucosa of the user's retromolar regions of the upper jaw.

6. The echography apparatus according to claim 1, wherein the extra-buccal skull support is adjustable in height.

7. The echography apparatus according to claim 1, wherein the extra-buccal skull support is formed of flexible plastic.

8. The echography apparatus according to claim 1, wherein the extra-buccal skull support is adjustable via a telescopic adjustment so as to fit snugly around the user's head.

9. The echography apparatus according to claim 1, wherein the intra-buccal maxillary support is adjustable in length in a horizontal plane.

10. The echography apparatus according to claim 1, wherein the intra-buccal maxillary support is adjustable in length in a horizontal plane via a telescopic adjustment so as to fit around the upper dental arch in the horizontal plane.

11. The echography apparatus according to claim 1, wherein the intra-buccal maxillary support is formed of flexible plastic.

12. The echography apparatus according to claim 1, wherein the maxillary intra-buccal support is generally semicircular in shape.

* * * * *

UNITED STATES PATENT AND TRADEMARK OFFICE
CERTIFICATE OF CORRECTION

PATENT NO. : 8,366,626 B2  
APPLICATION NO. : 12/664772  
DATED : February 5, 2013  
INVENTOR(S) : Edward W. Lee et al.

Page 1 of 1

It is certified that error appears in the above-identified patent and that said Letters Patent is hereby corrected as shown below:

Under the heading "OTHER PUBLICATIONS" on the Title page, replace "Hossein" with -- Kafai --.

Signed and Sealed this
Twentieth Day of August, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,366,626 B2  Page 1 of 1
APPLICATION NO. : 12/664772
DATED : February 5, 2013
INVENTOR(S) : Hossein Kafai El-Khorassani It is certified that error appears in the above-identified patent and that said Letters Patent is hereby corrected as shown below:

Title Page, item (56), under the heading "OTHER PUBLICATIONS" replace "Hossein" with -- Kafai --.

Signed and Sealed this
Twenty-eighth Day of July, 2015

Michelle K. Lee
*Director of the United States Patent and Trademark Office*